US011230519B2

(12) United States Patent
Wietelmann et al.

(10) Patent No.: US 11,230,519 B2
(45) Date of Patent: Jan. 25, 2022

(54) LOW-VISCOSITY SOLUTIONS OF ALKALINE-EARTH METAL ALKOXIDES IN APROTIC SOLVENTS, METHOD FOR THE PRODUCTION OF SAME AND USE FOR THE PRODUCTION OF ZIEGLER-NATTA CATALYSTS

(71) Applicant: ALBEMARLE GERMANY GMBH, Frankfurt am Main (DE)

(72) Inventors: Ulrich Wietelmann, Friedrichsdorf (DE); Ute Emmel, Frankfurt am Main (DE); Armin Stoll, Hirschberg an der Bergstraße (DE); Florian Kiefer, Goslar (DE)

(73) Assignee: Albemarle Germany GmbH

( * ) Notice: Subject to any disclaimer, the term of this patent is extended or adjusted under 35 U.S.C. 154(b) by 195 days.

(21) Appl. No.: 16/717,242

(22) Filed: Dec. 17, 2019

(65) Prior Publication Data

US 2020/0123086 A1     Apr. 23, 2020

Related U.S. Application Data

(62) Division of application No. 15/503,186, filed as application No. PCT/EP2015/068513 on Aug. 12, 2015, now Pat. No. 10,544,074.

(30) Foreign Application Priority Data

Aug. 12, 2014 (DE) .................. 10 2014 215 919.9
Aug. 13, 2014 (DE) .................. 10 2014 216 067.7
Nov. 26, 2014 (DE) .................. 10 2014 224 139.1

(51) Int. Cl.
| C07C 31/30 | (2006.01) |
| C07F 3/02  | (2006.01) |
| C07C 29/68 | (2006.01) |
| C07C 29/70 | (2006.01) |

(52) U.S. Cl.
CPC .............. *C07C 31/30* (2013.01); *C07C 29/68* (2013.01); *C07C 29/70* (2013.01); *C07F 3/02* (2013.01)

(58) Field of Classification Search
None
See application file for complete search history.

(56) References Cited

U.S. PATENT DOCUMENTS

| 3,903,019 | A  | 9/1975  | Hargis et al. |
| 4,133,824 | A  | 1/1979  | Malpass et al. |
| 4,410,742 | A  | 10/1983 | Mueller |
| 4,634,786 | A  | 1/1987  | Kamienski |
| 6,734,134 | B1 | 5/2004  | Gray et al. |
| 2012/0149553 | A1 | 6/2012 | Wietelmann et al. |
| 2015/0291708 | A1 | 10/2015 | Wietelmann et al. |

FOREIGN PATENT DOCUMENTS

| EP | 0027577 A1    | 4/1981  |
| EP | 0 156 512 B1  | 6/1989  |
| EP | 1 031 580 A1  | 8/2000  |
| WO | 1985/02176 A1 | 5/1985  |
| WO | 2010/146122 A1| 12/2010 |

OTHER PUBLICATIONS

J N. Manual, copyright 2009, Part III, Classification Procedures, Test Methods and Criteria Relating to Class 2, Class 3, Class 4, Division 5.1, Class 8 and Class 9, pp. 319-401.

*Primary Examiner* — Yun Qian
(74) *Attorney, Agent, or Firm* — McGlinchey Stafford, PLLC

(57) ABSTRACT

One or more concentrated low-viscosity solutions of alkaline earth alkoxide compounds $M(OCH_2R^6)_{2-a-b}(OR^7)_a[O(CHR^8)_nOR^9]_b$ in mixture with a metal alkyl compound $M(R^{10}R^{11})$ in an aprotic solvent and related methods are disclosed herein.

14 Claims, No Drawings

LOW-VISCOSITY SOLUTIONS OF ALKALINE-EARTH METAL ALKOXIDES IN APROTIC SOLVENTS, METHOD FOR THE PRODUCTION OF SAME AND USE FOR THE PRODUCTION OF ZIEGLER-NATTA CATALYSTS

CROSS-REFERENCE TO RELATED APPLICATIONS

This application is a divisional of U.S. patent application Ser. No. 15/503,186, filed Feb. 10, 2017, which is a National Stage entry of International Patent Application PCT/EP2015/068513, filed on Aug. 12, 2015, which claims priority from German Patent Application No. 10 2014 215 919.9, filed Aug. 12, 2014, German Patent Application No. 10 2014 216 067.7, filed Aug. 13, 2014, and German Patent Application No. 10 2014 224 139.1, filed Nov. 26, 2014. Each patent application identified above is incorporated here by reference in its entirety.

Magnesium alkoxides are needed for synthesis of supported olefin polymerization catalysts of the Ziegler-Natta type, among other things. To do so, according to the publication EP 1031580, insoluble alkoxides, such as magnesium ethoxide, are used in the form of spherical particles, which are converted to the active form by reaction with titanium chloride or some other compound (e.g., $Cp_2TiCl_2$) having titanium-halogen bonds:

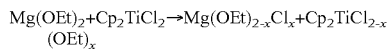

(x=0 to 2)

The publication WO 85/02176 describes another possibility for synthesis of supported Ziegler-Natta catalysts starting from soluble magnesium alkoxides. Whereas most magnesium alcoholates, such as the magnesium salts of methanol, ethanol, propanol, isopropanol, tert-butanol, etc., are insoluble in aprotic solvents, many Mg compounds of primary alcohols having a branch in position 2 have proven to be soluble in hydrocarbons. It is known from the publication WO 85/02176 that the magnesium salts of 2-methyl-1-pentanol or of 2-ethyl-1-hexanol in concentrations of 1.3 mol/L, for example, will dissolve in cyclohexane. Mixed Mg alkoxides, i.e., those with two different alkoxide radicals $Mg(OR^1)_n(OR^2)_{2-n}$, may be soluble in hydrocarbons if the corresponding alcohol $R^1OH$ is a primary alcohol with branching in position 2, and the corresponding alcohol $R^2OH$ is a secondary alcohol, for example.

One disadvantage of hydrocarbon solutions which do not have any other dissolved metal except for magnesium is their relatively high viscosity. In addition, it is impossible to prepare such solutions directly by reacting magnesium metal with the alcohol in the desired hydrocarbon without adding any additives, which cause problems. To permit a direct reaction at all, the magnesium metal must be activated, which can be achieved by etching with iodine. With this measure, the reaction rate is still very low, even when using highly reactive Mg powder. Thus, the document EP 0156512 describes the preparation of a dilute solution of magnesium bis(2-ethylhexoxide) in dodecane by using iodine. A 10-hour reaction time is necessary at a reaction temperature of 145° C., and the product is obtained in the form of a viscous solution. Therefore, to avoid extremely long reaction times, magnesium alcoholate solutions in general are therefore prepared by starting with commercially available dialkyl magnesium compounds ($R_2Mg$). However, this synthesis route has the disadvantage that a relatively expensive magnesium source (namely the $R_2Mg$ compounds whose synthesis requires haloalkanes) is used. In addition, it implies a stipulation of certain solvents, namely saturated hydrocarbons. Dialkyl magnesium compounds, for example, dibutyl magnesium, butylethyl magnesium and butyloctyl magnesium are available commercially only in saturated hydrocarbons such as hexane or heptane.

Furthermore, saturated hydrocarbons ($R^3H$ and $R^4H$, for example, butane or octane) are unavoidably formed in alcoholysis according to the equation:

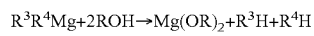

It is therefore impossible to synthesize magnesium alcoholates in purely aromatic solvents, such as toluene or ethylbenzene, starting from commercially available dialkyl magnesium compounds.

Another synthesis variant for producing soluble alkaline earth alcoholates consists of re-alcoholization of insoluble alkaline earth alcoholates synthesized from readily volatile alcohols (for example, ethanol) with a higher boiling alcohol, for example:

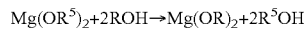

One disadvantage is the relatively high, cost-intensive effort involved in this method because the alcoholate $Mg(OR^5)_2$ must first be synthesized from the volatile alcohol $R^5OH$ and magnesium metal and isolated, then reacted with a less volatile alcohol, for example, 2-ethylhexanol, and then the more volatile alcohol $R^5OH$ must be removed by distillation, for example.

The relatively high viscosity of magnesium alkoxide solutions is caused by association phenomena. It is known from the document U.S. Pat. No. 6,734,134 that the viscosity can be reduced by adding alkyl aluminum compounds. The preferred ratio between the alkyl aluminum compound and Mg alcoholate is between 0.001:1 and 1:1, more preferably between 0.01 and 0.1:1 and most especially preferably between 0.03 and 0.05:1.

Finally, it is known from the document WO 2010/146122 that mixed alkaline earth alkoxide compounds $M(OCH_2R^6)_{2-x}(OR^7)_x$ can be produced in mixture with an aluminum compound $Al(OCH_2R^6)_{3-y}(OR^7)_y$ in aprotic solvents, starting from an alkaline earth metal and two different alcohols, wherein M is an alkaline earth metal selected from Mg, Ca, Ba, Sr;

$OCH_2R^6$ is an alkoxide radical consisting of at least 3 carbon atoms and at most 40 carbon atoms with a branch in position 2 relative to the O function, i.e., $R^6$=—$CHR^8R^9$ where $R^8$, $R^9$ independently of one another denote $C_1$-$C_{18}$ alkyl radicals;

$R^7$ is an alkyl radical with 2-15 carbon atoms, which is either linear or has a branch at ≥position 3 (relative to the O function);

and the sum of x plus y gives a number between 0.01 and 0.8, preferably between 0.02 and 0.3 and especially preferably between 0.03 and 0.2.

The product solutions prepared with the help of this method have relatively high concentrations of alkaline earth alkoxide compounds (i.e., $c_{Mg}$>0.5 mol/kg), but in the case of products with relatively low concentrations of viscosity-reducing Al compounds (≤3 mol %, based on the dissolved alkaline earth metal concentration) are still unsatisfactorily high, typically with ≥1000 cP at room temperature (RT). According to the document U.S. Pat. No. 6,734,134 a low Al concentration is crucial for use as a Ziegler-Natta catalyst support material according to the document U.S. Pat. No. 6,734,134.

Furthermore, dialkyl magnesium compounds such as butylethyl magnesium or dibutyl magnesium can be used directly for synthesis of Ziegler-Natta catalyst support materials (chemically $MgCl_2$). However, one disadvantage of the use of dialkyl magnesium compounds is their relatively high production cost and the fact that hydrocarbon solutions of such metal organyls are pyrophoric. These pyrophoric properties require the use of special shipping, storage and handling regulations which are a disadvantage.

Mixtures of dialkoxy magnesium and dialkyl magnesium compounds are also known. Thus Example XVIII of U.S. Pat. No. 4,634,786 describes the synthesis of a heptane-cyclohexane solution containing a 1:1 complex consisting of magnesium 2-methyl-1-pentoxide and dibutyl magnesium. However, exact stoichiometric amounts of dialkyl magnesium compound and alcohols are used in the other example of the aforementioned patent, so that $Mg(OR^1R^2)$ compounds having an exact stoichiometric composition (i.e., those that are free of excess $R_2Mg$) are formed. One can find in Examples I, II, III references to the fact that it is favorable from the standpoint of viscosity to use an excess of alcohol. Thus, for example, the viscosity of the product solution having a stoichiometric composition is "perceptibly" reduced by adding approx. 5 mol % 2-methyl-1-pentanol in Example 1.

The invention has taken as its object to find concentrated alkaline earth metal oxide compounds in aprotic solvents, in particular hydrocarbons that have a low Al concentration (e.g., <5 mol % based on the Mg content), which have a low viscosity (e.g., <500 cP at RT) at the same time and are not pyrophoric and also to provide methods for their synthesis.

This object is achieved by making available mixtures of alkaline earth alkoxide compounds $M(OCH_2R^6)_{2-a-b}(OR^7)_a[O(CHR^8)_nOR^9]_b$ and a metal alkyl compound $M(R^{10}R^{11})$ with an alkaline earth metal concentration in the range of 0.2 to 1.8 mmol/g in aprotic solvents, wherein M is an alkaline earth metal selected from Mg, Ca, Ba, Sr;
$OCH_2R^6$ is an alkoxide radical consisting of at least 3 and at most 40 carbon atoms with a branch in position 2 relative to the O function, i.e., $R^6$=—$CHR^{12}R^{13}$ with $R^{12}$, $R^{13}$ denoting independently of one another alkyl radicals $C_1$-$C_{18}$;
$R^7$ is an alkyl radical with 2-15 carbon atoms which is either linear or has a branch in ≥position 3 (relative to the O function)
$R^8$ is an alkyl radical with 1 to 6 carbon atoms, which is either linear or has a branch at ≥position 3 (relative to the O function)
$R^9$ is an alkyl radical with 2-15 carbon atoms which is either linear or has a branch
$R^{10}$ and $R^{11}$ are any alkyl radicals with 1-15 carbon atoms
n is an integer from 1 to 4
a+b≤2 wherein a and b may assume values of 0 to 2 and the molar ratio $M(OCH_2R^6)_{2-a-b}(OR^7)_a[O(CHR^8)_nOR^9]_b$ to $M(R^{10}R^{11})$ is from 99.5:0.5 to 60:40, preferably from 99:1 to 70:30 and especially preferably from 95:5 to 80:20.

It has surprisingly been found that by adding even small amounts of alkaline earth metal alkyls to solutions of alkaline earth alkoxide compounds in aprotic solvents, their viscosity can be reduced drastically. This is in contrast with the technical teaching known from U.S. Pat. No. 4,634,786 that only the addition of further alcohol to magnesium alkoxide solutions having a stoichiometric composition has a viscosity-reducing effect.

The solutions according to the invention contain from 0.1 to 30 mol %, preferably 1 to 20 mol % and especially preferably 3-15 mol % active base $R_2Mg$, determined by direct titration with sec-butanol and biquinoline as an indicator and based on the total amount of alkaline earth metal M in solution.

In addition, an aluminum compound $Al(OCH_2R^6)_{3-c-d}(OR^7)_c[O(CHR^8)_nOR^9]_d$ is preferably contained in the solutions according to the invention, wherein
$OCH_2R^6$ is an alkoxide radical consisting of at least 3 and at most 40 carbon atoms with a branch in position 2 relative to the O function, i.e., $R^6$=—$CHR^{12}R^{13}$ where $R^{12}$, $R^{13}$=independently of one another alkyl radicals $C_1$-$C_{18}$;
$R^7$ is an alkyl radical with 2-15 carbon atoms which is either linear or has a branch at ≥position 3 (relative to the O function);
$R^8$ is an alkyl radical with 1 to 6 carbon atoms which is either linear or has a branch at ≥position 3 (relative to the O function);
$R^9$ is an alkyl radical with 2-15 carbon atoms which is either linear or has a branch
n=an integer from 1 to 4,
c+d≤3 and both c and d may assume values of 0 to 3 and wherein the amount of aluminum compound $Al(OCH_2R^6)_{3-c-d}(OR^7)_c[O(CHR^8)_nOR^9]_d$ based on the dissolved alkaline earth metal is in the range of 0 to approx. 20 mol %, preferably 0.2 to 5 mol %, especially preferably 0.5 to 4 mol %.

The aprotic solvent is or contains either one or more aliphatic compounds with 5 to 20 carbon atoms, wherein both cyclic and open chain compounds are possible. Preferred compounds include cyclohexane, methyl cyclohexane, hexane, heptane, octane, nonane, decane, dodecane, decalin as well as commercial boiling cuts (gasoline fractions).

The aprotic solvent may additionally contain or consist of aromatics. Preferred aromatics include benzene, toluene, ethylbenzene, xylenes and cumene.

In another embodiment of the invention, the alkaline earth alkoxide solution according to the invention still contains polar aprotic solvents such as ether or tertiary amines.

The alcohol ($HOCH_2R^6$) which is branched in position 2 is especially preferably selected from the group consisting of isobutanol, 2-methyl-1-pentanol, 2-ethyl-1-butanol, 2-ethyl-1-pentanol, 2-ethyl-4-methyl-1-pentanol, 2-propyl-1-heptanol, 2-methyl-1-hexanol, 2-ethylhexanol and 2-ethyl-5-methyl-1-octanol or any mixture of at least two of the alcohols listed. The primary alcohol ($HOR^7$) is preferably selected from the group consisting of ethanol, propanol, butanol, pentanol, hexanol, octanol, decanol, dodecanol, 3-methylbutan-1-ol or any mixture of at least two of the alcohols listed. The alcohol $HO(CHR^8)_nOR^9$ which contains an alkoxy function is preferably a $C_2$-$C_4$ glycol monoethers, for example, 2-ethoxyethanol, 3-ethoxy-1-propanol, 3-ethoxy-1-butanol, 2-(2-ethylhexoxy)ethanol, 2-butoxyethanol, 2-hexyloxyethanol as well as 1,3-propylene glycol monobutyl ether or any mixture of at least two of the alcohols listed.

The products according to the invention can be synthesized, for example, according to two different methods.

The first method begins with commercial alkaline earth metal, preferably magnesium metal which is preferably in the form of a powder, granules or shavings. The metal is placed in an anhydrous aprotic solvent, preferably aromatic or aliphatic hydrocarbons, in an inertized stirred container, dried and provided with a protective gas (nitrogen or argon). Then an alkyl aluminum compound, e.g., trialkyl aluminum such as triethyl aluminum, tributyl aluminum, an alkyl aluminum hydride, such as dibutyl aluminum hydride, an alkyl aluminum halide, such as dibutyl aluminum chloride or an alkoxyaluminum compound, such as diethyl aluminum ethoxide may be added. In general the molar ratio of alkyl aluminum compound to the alcohols is from 0 to 0.1:1, preferably from 0.005 to 0.04:1. The aluminum compound may also be added entirely or partially after the alcohol or to the alcohol(s).

Then the desired alcohols, i.e., the alcohol $HO(CHR^8)_nOR^9$ and/or a branched alcohol $HOCH_2R^6$ and/or an unbranched primary alcohol with 2-15 carbon atoms ($HOR^7$) or one having a branch at ≥position 3 is/are added either as a mixture or one after the other. Preferably the primary alcohol $R^7OH$ is added first, then the alcohols selected from the other substance groups are added. This addition may take place at temperatures between 0 and 180° C., preferably between approx. 40 and 140° C. The addition most especially preferably takes place at the boiling point of the solvent being used, i.e., in the case of toluene, for example, at approx. 110° C. The reaction time depends on the reactivity of the alkaline earth metal that is used, in particular that of magnesium as well as the acidity of the alcohol used, the stoichiometric ratio between the alkaline earth metal, in particular magnesium, and the alcohols as well as the reaction temperature. If the alkaline earth metal in particular the magnesium is used in excess (preferably 1 to 300 mol %, especially preferably from 10 to 100 mol %), then a reaction time of 1 to 6 hours is sufficient in the reflux procedure. The reaction is preferably continued until practically all the alcohol has reacted, i.e., its concentration is <0.01 mmol/g, preferably <0.001 mmol/g.

After the end of the reaction, which can be recognized by the subsidence of the hydrogen stream, the solution of an alkaline earth metal alkyl compound, e.g., $MgR^{10}R^{11}$ is added to the relatively viscous reaction mixture. Another brief increase in viscosity is usually observed, but it is reversed to the opposite after adding a few mol % $MgR^{10}R^{11}$, i.e., the viscosity of the reaction solution surprisingly changes to a low viscosity rather suddenly; depending on the alcohols used as well as other parameters, this effect occurs after adding 1-20 mol % metal alkyl compound. However, further addition of $MgR^{10}R^{11}$ causes only a minor further decline in viscosity, which is insignificant in terms of handling technology. For example, if an approx. 30 wt % heptane solution of magnesium bis(2-ethylhexoxide) containing barely 3 mol % Al is mixed with 9 or 4 mol % of a dialkyl magnesium compound, for example, butylethyl magnesium, then the viscosity drops from ≥1000 cP to approx. 50 or 100 cP at RT.

The second preferred preparation method starts with solutions of dialkyl magnesium compounds in aprotic solvents. The desired alcohol(s) is/are added to these solutions in a stoichiometric amount leading to the products according to the invention. The substances may be added in any order. A prefabricated alcohol mixture may also be used. It is also possible to start with the alcohol or alcohols preferably in mixture with aprotic solvent and then add the dialkyl magnesium component. Finally, a simultaneous dosing in the solvent supplied is also conceivable.

The products produced by the method according to the invention surprisingly have a very low viscosity, despite the high alkaline earth metal concentration of ≥0.5 mol/kg, preferably ≥1.0 mol/kg. The alkaline earth metal concentrations are preferably in the range of approx. 0.4 to 1.6 mmol/g, especially preferably from 0.7 to 1.4 mmol/g. The viscosities measured at room temperature are generally less than 300 cP, preferably less than 200 cP, especially preferably less than 100 cP at Mg concentrations ≥1 mmol/g and ≤1.5 mmol/g.

The dissolved aluminum content is in the range of 0 to approx. 20 mol %, preferably in the range of 0.2 to 15 mol %, especially preferably in the range of 0.5 to 4 mol %, based on the dissolved alkaline earth metal.

The products according to the invention are used to produce polymerization catalysts, in particular heterogenized polyolefin catalysts of the Ziegler-Natta type. Furthermore, they may be used as bases, for example, in organic synthesis.

EXAMPLES

All the reactions were carried out in dry glass equipment inertized with argon. Commercial magnesium shavings were used. The concentrations of Mg and Al were measured by means of ICP (inductively-coupled plasma).

The active base is determined by direct titration with 1M 2-butanol solution in hexane against 2,2-biguinoline as the indicator. Color change from red to gray.

Example 1

Preparation of a 35% Solution of Magnesium bis(2-ethylhexoxide) in Mixture with 6 Mol % Dibutyl Magnesium in Heptane Using a 0.5 L double jacketed glass reactor with a reflux condenser and a dropping funnel, 32.0 g magnesium shavings and 352 g heptane were placed as starting materials. Then 11.3 g of a 20 wt % solution of triethyl aluminum in heptane, 1.8 g ethanol and 171.9 g 2-ethylhexanol were added and heated to the boiling point, then refluxed for 4 hours, whereupon 14.6 L gas was formed and a viscous solution of magnesium bis(2-ethylhexoxide) was obtained. A sample was taken and its viscosity was determined (1025 cP at 25° C.).

The reaction mixture was then cooled to approx. 80° C. and 54.6 g of a dibutyl magnesium solution in hexane (Mg=1.08 mmol/g) was added. After this addition, the resulting solution had a low viscosity and was easy to handle. The light gray suspension was syphoned off and filtered, yielding 579 g of a non-viscous liquid with a magnesium content of 1.22 mmol/g. The product solution in turn contained 0.030 mmol/g aluminum and had an active base content of 0.15 mmol/g (corresponding to 0.075 mmol/g $Bu_2Mg$, approx. 6 mol %).
Yield: 98% of the theoretical
Viscosity (Brookfield, 25° C.): 33 cP
In the UN test N.2, N.3, the product solution was found to be non-pyrophoric.

Example 2

Preparation of a 29% Magnesium Decanolate Solution in Hexane in Mixture with 14 Mol % Dibutyl Magnesium Using a 0.5 liter double jacketed glass reactor with a reflux condenser and dropping funnel, 82.0 g of a dibutyl magnesium solution in hexane (Mg=1.11 mmol/g, 91 mmol) was added as the starting mixture. Then 23.6 g n-decanol (149 mmol) was added while stirring vigorously. A gelatinous reaction product was formed temporarily at the addition point, but it completely dissolved as stirring was continued. After the end of dosing, a non-viscous colorless and clear solution was obtained.
Yield: 104 g solution
Total magnesium content: 0.88 mmol/g
Active base unit: 0.24 mmol/g
Viscosity (Brookfield, 25° C.): 4.8 cP
In the UN test N.2, N.3, the product solution was found to be non-pyrophoric.

Comparative Example 1

Preparation of an Approx. 30% Magnesium Decanolate Solution in Hexane

Using a 0.5 liter double jacketed glass reactor with a reflux condenser and dropping funnel, 85.0 g of a dibutyl magnesium solution in hexane (Mg=1.11 mmol/g, 94 mmol) was added. Then 31.2 g n-decanol (197 mmol) was added while stirring vigorously. After adding approx. 90% of the total amount of alcohol, the gelatinous phase formed at the addition point would always dissolve more slowly and then would no longer dissolve at all. After the end of dosing, a stiff gel was formed and could not be liquefied even by heating (approx. 80° C.).
No sample could be taken by syringe due to the gelatinous consistency.

Example 3

Preparation of a 35% Solution of Magnesium bis(2-ethylhexoxide)/Magnesium Decanolate (75:25) in Mixture with Approx. 5 Mol % Butylethyl Magnesium in Heptane Using a 0.5 liter double-jacketed glass reactor with a reflux condenser and a dropping funnel, 32.0 g magnesium shavings and 352 g heptane were placed as starting materials. Then 11.3 g of a 20 wt % solution of triethyl aluminum in heptane, 1.8 g ethanol and a mixture of 128.9 g 2-ethylhexanol and 52.2 g 1-decanol were added and heated to the boiling point. Refluxing was continued for 3.5 hours, whereupon 16.0 L gas had formed and the viscous solution of the mixed magnesium alkoxide was obtained. A sample was taken and its viscosity was determined (3800 cP at 25° C.).
The solution was cooled to 100° C. and 55.1 g of a butylethyl magnesium solution in heptane (Mg=1.09 mmol/g) was added. After the addition, a low viscosity solution that could be handled easily was obtained. The light gray suspension was syphoned and filtered, and 534 g of a non-viscous liquid with a magnesium content of 1.19 mmol/g was isolated. The product solution still contained 0.033 mmol/g aluminum and had an active base content of 0.11 mmol/g (corresponding to 0.055 mmol/g BuMgEt, 4.6 mol %).
Yield: 88% of theoretical
Viscosity (Brookfield, 25° C.): 16 cP
In the UN test N.2, N.3, the product solution was found to be non-pyrophoric.

Example 4

Preparation of a 34% Solution of Magnesium bis(2-ethylhexoxide) in Mixture with 5 Mol % Butylethyl Magnesium in Toluene Using a 0.5 liter double-jacketed glass reactor with a reflux condenser and a dropping funnel, 32.0 g magnesium shavings and 352 g toluene were placed as starting materials. The 9.0 g of a 25 wt % solution of triethyl aluminum in toluene, 1.8 g ethanol and 171.9 g 2-ethylhexanol were added and the mixture was heated to the boiling point. Refluxing was continued for just 4 hours, whereupon 16.4 L gas had formed and a viscous solution of the magnesium alkoxide was obtained.
Then the mixture was cooled to 100° C. and 56.5 g of a dibutyl magnesium solution in heptane (Mg=1.08 mmol/g) was added. After this addition, a low viscosity solution that could be handled easily was obtained. The light gray suspension was syphoned off and filtered, and 576 g of a non-viscous liquid with a magnesium content of 1.21 mmol/g was isolated. The product solution again contained 0.030 mmol/g aluminum and had an active base content of 0.13 mmol/g (corresponding to 0.065 mmol/g BuMgEt, 5.4 mol %).
Yield: 97% of the theoretical
Viscosity (Brookfield, 25° C.): 94 cP
In the UN test N.2, N.3, the product solution was found to be non-pyrophoric.

Comparative Example 1 and a comparison of the viscosity data before and after addition of dialkyl magnesium solution in Examples 1 and 3 show the positive effect achieved by adding dialkyl magnesium solution to magnesium alkoxide solutions (Examples 1 and 3) and/or using a substoichiometric amount of alcohol in the reaction with dialkyl magnesium solution (Example 2 and Comparative Example 1).

Whereas all the product solution prepared according to the invention with Mg concentrations between 0.88 and 1.22 mmol/g and Al concentrations of ≤3 mol % could be handled very well and had a low viscosity (viscosity at 25° C. <100 cP), the product solutions containing dialkyl magnesium were extremely viscous: the viscosities of the liquid products were between >1000 cP and 3800 cP. If no alcohol branched in position 2 ($HOCH_2R^6$ consisting of at least 3 carbon atoms and at most 40 carbon atoms with a branch in position 2 relative to the O function, i.e., $R^6$=—$CHR^{12}R^{13}$ where $R^{12}$, $R^{13}$=independently of one another alkyl radicals $C_1$-$C_{18}$) is used but instead only unbranched alcohols are used, the result of a complete reaction and/or use of a slight excess of alcohol (Comparative Example 1) is a gelatinous product that is not comparable or transferable in any other way. However, in the presence of approx. 14 mol % dibutyl magnesium, a watery, low-viscosity product is obtained. Such a product cannot be produced according to U.S. Pat. No. 4,634,786 because, according to this prior art document, "(a) aliphatic 2-alkyl-substituted primary monoalcohols; or (b) mixtures of the aforementioned (a) alcohols with $C_3$-$C_{12}$ aliphatic secondary or tertiary alcohols; or (c) mixtures of said (a) alcohols with $C_1$-$C_{12}$ aliphatic primary linear unsubstituted alcohols; wherein the molecular ratios of said (a) alcohols to said (b) alcohols and of said (a) alcohols to said (c) alcohols (amounts to) 1 for said (a) alcohols to 0.1 to 2 of said (b) alcohols and said (c) alcohols," i.e., in each case, (a) alcohols branched in position 2 are needed.

All the product solutions according to the invention are non-pyrophoric.

That which is claimed is:
1. A method for synthesis of alkaline earth alkoxide compounds $M(OCH_2R^6)_{2-a-b}(OR^7)_a[O(CHR^8)_nOR^9]_b$ in mixture with an alkaline earth metal alkyl compound $M(R^{10}R^{11})$, the method comprising
(A) mixing one or more alkaline earth metals, an aprotic solvent, one or more alkyl aluminum compounds, and one or more alcohols at a temperature in the range of 0°

C. and 180° C. to produce a mixture comprising the alkaline earth alkoxide compounds $M(OCH_2R^6)_{2-a-b}(OR^7)_a[O(CHR^8)_nOR^9]_b$;

wherein:
(i) M is an alkaline earth metal selected from the group consisting of Mg, Ca, Ba, and Sr;
(ii) $OCH_2R^6$ is an alkoxide radical having 3 to 40 carbon atoms with a branch in position 2 relative to the O function;
(iii) $R^7$ is an alkyl radical having 2 to 15 carbon atoms, which is either linear or has a branch in ≥position 3 relative to the O function;
(iv) $R^8$ is an alkyl radical having 1 to 6 carbon atoms, which is either linear or has a branch at ≥position 3 relative to the O function;
(v) $R^9$ is an alkyl radical having 2 to 15 carbon atoms, which is either linear or has a branch;
(vi) $R^{10}$ and $R^{11}$ each are an alkyl radical having 1 to 15 carbon atoms;
(vii) n is an integer from 1 to 4;
(viii) a+b≤2 wherein a and b each have a value of 0 to 2; and (B) adding one or more alkaline metal alkyl compounds $M(R^{10}R^{11})$ to the mixture comprising the alkaline earth alkoxide compounds $M(OCH_2R^6)_{2-a-b}(OR^7)_a[O(CHR^8)_nOR^9]_b$, wherein the molar ratio of $M(OCH_2R^6)_{2-a-b}(OR^7)_a[O(CHR^8)_nOR^9]_b$ to $M(R^{10}R^{11})$ is from 99.5:0.5 to 60:40.

2. The method according to claim 1 wherein the one or more alkyl aluminum compounds are selected from the group consisting of alkyl aluminum compounds, alkylalkoxy aluminum compounds, alkyl aluminum halide compounds, alkyl aluminum hydride compounds, wherein the aluminum concentration based on the dissolved alkaline earth metal is in the range of 0 mol % to about 20 mol %.

3. The method according claim 2, wherein the aluminum concentration based on the dissolved alkaline earth metal is in the range of 0.2 mol % to about 15 mol %.

4. The method according claim 2, wherein the aluminum concentration based on the dissolved alkaline earth metal is in the range of 0.5 mol % to about 4 mol %.

5. The method according to claim 2 wherein in step (B) the molar ratio of $M(OCH_2R^6)_{2-a-b}(OR^7)_a[O(CHR^8)_nOR^9]_b$ to $M(R^{10}R^{11})$ is from 99:1 to 70:30.

6. The method according to claim 2 wherein in step (B) the molar ratio of $M(OCH_2R^6)_{2-a-b}(OR^7)_a[O(CHR^8)_nOR^9]_b$ to $M(R^{10}R^{11})$ is from 95:5 to 80:20.

7. The method according to claim 2, wherein step (B) occurs after the end of the reaction in step (A).

8. The method according to claim 2 wherein in step (A) half of the molar ratio of the total number of moles of all alcohols to the alkaline earth metal alkyl compound is from 99.5:0.5 to 60:40.

9. The method according to claim 2 wherein in step (A) half of the molar ratio of the total number of moles of all alcohols to the alkaline earth metal alkyl compound is from 99:1 to 70:30.

10. The method according to claim 2 wherein in step (A) half of the molar ratio of the total number of moles of all alcohols to the alkaline earth metal alkyl compound is from 99:5 to 80:20.

11. The method according to claim 1, wherein the aprotic solvent is either (i) an aliphatic solvent selected from the group consisting of cyclohexane, methyl cyclohexane, hexane, heptane, octane, nonane, decane, dodecane, decalin and gasoline fractions; or (ii) an aromatic solvent selected from the group consisting of benzene, toluene, ethylbenzene, xylenes and cumene.

12. The method according to claim 1, wherein the one or more alcohols are selected from the group of $HOCH_2R^6$, $HOR^7$, $HO(CHR^8)_nOR^9$, and any combination of two or more of the foregoing, wherein $HO(CHR^8)_nOR^9$ is selected from the group consisting of 2-ethoxyethanol, 3-ethoxy-1-propanol, 3-ethoxy-1-butanol, 2-(2-ethylhexoxy)ethanol, 2-butoxyethanol, 2-hexyloxyethanol, 1,3-propylene glycol monobutyl ether, and any combination of two or more of the foregoing;

wherein $HOCH_2R^6$ is branched in position 2 and is selected from the group consisting of isobutanol, 2-methyl-1-pentanol, 2-ethyl-1-butanol, 2-ethyl-1-pentanol, 2-ethyl-4-methyl-1-pentanol, 2-propyl-1-heptanol, 2-methyl-1-hexanol, 2-ethylhexanol and 2-ethyl-5-methyl-1-octanol, and any combination of two or more of the foregoing; and wherein $HOR^7$ is selected from the group consisting of ethanol, propanol, butanol, pentanol, hexanol, octanol, decanol, dodecanol, 3-methylbutan-1-ol, and any combination of two or more of the foregoing.

13. The method according to claim 1, wherein in step (A) the reaction conditions comprise a temperature in the range of about 40° C. and 140° C.

14. The method according to claim 1, wherein in step (A) the reaction conditions comprise a temperature that is at the boiling point of the aprotic solvent.

* * * * *

UNITED STATES PATENT AND TRADEMARK OFFICE
CERTIFICATE OF CORRECTION

PATENT NO. : 11,230,519 B2  
APPLICATION NO. : 16/717242  
DATED : January 25, 2022  
INVENTOR(S) : Ulrich Wietelmann et al.

Page 1 of 1

It is certified that error appears in the above-identified patent and that said Letters Patent is hereby corrected as shown below:

On the Title Page

Item (56) under the heading "OTHER PUBLICATIONS", the literature reference reads "J. N. Manual, copyright 2009, Part III, Classification Procedures, Test Methods and Criteria Relating to Class 2, Class 3, Class 4, Division 5.1, Class 8 and Class 9, pp. 319-401." and should read -- U. N. Manual, copyright 2009, Part III, Classification Procedures, Test Methods and Criteria Relating to Class 2, Class 3, Class 4, Division 5.1, Class 8 and Class 9, pp. 319-401. --.

Signed and Sealed this  
Twenty-second Day of March, 2022

Drew Hirshfeld  
*Performing the Functions and Duties of the*  
*Under Secretary of Commerce for Intellectual Property and*  
*Director of the United States Patent and Trademark Office*